US00RE34335E

United States Patent [19]

Butler et al.

[11] E Patent Number: Re. 34,335

[45] Reissued Date of Patent: Aug. 3, 1993

[54] SINGLE USE SYRINGE

[75] Inventors: John H. A. Butler, 3 St. Mervyns Avenue, Double Bay, New South Wales 2028; Alexander S. Richardson, Chatswood, both of Australia

[73] Assignee: John Henry Adam Butler, Double Bay, Australia

[21] Appl. No.: 761,169

[22] PCT Filed: Oct. 14, 1988

[86] PCT No.: PCT/AU88/00402

§ 371 Date: Jul. 10, 1989

§ 102(e) Date: Jul. 10, 1989

[87] PCT Pub. No.: WO89/03698

PCT Pub. Date: May 5, 1989

Related U.S. Patent Documents

Reissue of:

[64] Patent No.: 4,941,879
Issued: Jul. 17, 1990
Appl. No.: 373,291
Filed: Jun. 14, 1989

[30] Foreign Application Priority Data

Oct. 14, 1987 [AU] Australia ..... PI4881
Mar. 29, 1988 [AU] Australia ..... PI7493
Jul. 29, 1988 [AU] Australia ..... PI9554
Sep. 13, 1988 [AU] Australia ..... PJ0376

[51] Int. Cl.[5] ..... A61M 5/00
[52] U.S. Cl. ..... 604/110; 604/236
[58] Field of Search ..... 604/110, 187, 236, 237, 604/238, 246, 247, 249, 207

[56] References Cited

U.S. PATENT DOCUMENTS 4,233,975 11/1980 Yerman ..... 604/110
4,643,723 2/1987 Smit ..... 604/236
4,781,683 11/1988 Wozniak et al. ..... 604/236 X

FOREIGN PATENT DOCUMENTS 2632190 12/1989 France .

*Primary Examiner*—John D. Yasko
*Attorney, Agent, or Firm*—Christopher John Rudy

[57] ABSTRACT

A single use syringe [having] *has* an interacting piston and cylinder which cooperate to define a variable volume working space[,]; the syringe includes a valve body located in the chamber so as to divide the chamber into a first and second sub-chamber, *and* the valve body has valves which permit a liquid to be initially drawn into the syringe and then injected, but prevent a subsequent liquid being drawn into the syringe. *A valve for the syringe is also claimed.*

29 Claims, 7 Drawing Sheets

SINGLE USE SYRINGE

Matter enclosed in heavy brackets [ ] appears in the original patent but forms no part of this reissue specification; matter printed in italics indicates the additions made by reissue.

*This is a continuation (reissue) of U.S. Pat. No. 4,941,879 (Jul. 17, 1990) from U.S. application Ser. No. 07/373,291 filed Jun. 14, 1989 from PCT No. PCT/AU88/00402 filed Oct. 14, 1988.*

*FIELD*

The invention relates to hypodermic syringes *and valves,* and in particular to a single use hypodermic syringe *and syringe valve.*

*BACKGROUND*

Disposable syringes for which a single use is contemplated are well known as, for example, syringes for the injection of insulin in diabetics. Nothing, however, prevents there syringes from being reused (*re-used*) in a necessarily unsterile state. The result *is* that [contamination] syringes, when used *contaminated,* contribute to the spreading of disease such as AIDS or hepatitis.

Accordingly, *it* is desirable for syringes to be designed for a single use only, to inhibit their re-use and therefore the risk of using contaminated syringes.

Previously known single use syringes usually incorporate a modification of the piston of the syringe so that it is jammed in its fully inserted position adjacent the needle. These previously known devices have the disadvantage that the piston can become inadvertently jammed prior to a liquid being drawn into the cylinder of the syringe.

Described in British Patent No. 1,550,310 and French Patent No. 2,348,708 is a single use syringe. The syringe has a detachable piston which prevents re-use of the syringe. Once the piston has been moved to the minimum volume position, movement of the piston to again draw in a liquid is prohibited since the piston rod becomes detached from the piston head. This syringe suffers from the disadvantage that the piston can become detached from the piston rod, and the syringe cannot be operated to test whether the syringe has been correctly inserted. This is usually achieved by pulling back on the piston rod to draw into the syringe a small portion of blood. A similar syringe is disclosed in British Patent No. 2,015,883; again, this particular device shows a detachable piston which suffers from the disadvantages as discussed.

French Patent No. 2,298,340 discloses a single use syringe, with the piston being provided with a frangible diaphragm. Once the piston has been moved to the minimum volume position, a bar penetrates the diaphragm, preventing re-use of the syringe. *Disclosed in* British Patent No. 1,454,540 is *a syringe* of a similar construction, in that the piston is provided with a means of damaging the body of the syringe, preventing its re-use. Both [the] *of these* syringes suffer from the disadvantage that they do not enable operation of the syringe to test whether the needle has [be] *been* correctly located.

U.S. Pat. No. 3,951,146 discloses a single use syringe which employs a ratchet mechanism to prevent withdrawal of the piston. Again, this particular type of syringe does not enable testing to determine whether the needle has been correctly located. *The syringe of* British Patent No. 2,184,657 also uses a pawl to engage behind the piston to prevent re-use. It has the same disadvantages. *Syringes of* U.S. Pat. Nos. 3,478,937 and 3,890,971 also employ pawls or detent members which prevent reward movement of the piston. They suffer similar disadvantages.

U.S. Pat. No. 4,233,975 discloses a single use syringe with a plunger member which engages within a socket when the piston is moved to the minimum volume position. The plunger cannot be retracted, and *this* prevents re-use of the syringe.

U.S. Pat. No. 4,650,468 is similar to several of the above discussed patents since [it uses] *its syringe has* a plunger or piston which is automatically locked in a position preventing re-use.

The above discussed previously known single use syringes suffer from the further disadvantage in that they require the piston to be moved to the minimum volume [of] position before any action is taken to render the syringe inoperative.

*U.S. Pat. Nos. 4,643,723 and 4,781,683 may be of interest also. Note too, French Patent No. 2,632,190.*

*OBJECT*

It is the object of the present invention to overcome or substantially ameliorate the above disadvantages.

*INVENTION DISCLOSURE*

There is disclosed herein a single use syringe comprising:

- an inter-acting piston and cylinder defining a variable volume chamber within which a liquid to be injected is drawn;
- a needle mounting at one end of said cylinder, to receive a needle, a passage extending through said mounting enabling liquid communication between said cylinder and said needle;
- a piston rod attached to said piston and operable by a user to cause movement of said piston to vary the volume of said chamber;
- a valve means including a valve body located within said chamber between said mounting and said piston and dividing said chamber into a first sub-chamber located between said mounting and valve means, and a second sub-chamber located between said valve means and said piston, said valve body being movable longitudinally of said cylinder between a first position and a second position, and said valve means includes a first valve which, when said body is in said first position, permits flow from said first sub-chamber to said second sub-chamber and prevents flow from said second sub-chamber to said first sub-chamber, but when said body is in said second position, said first valve permits flow from said second sub-chamber to said first sub-chamber and prevents flow from said first sub-chamber to said second sub-chamber, and a second valve which, when said body is in said first position, permits flow from said first sub-chamber to said second sub-chamber, but prevents flow from said first sub-chamber to said second sub-chamber when said body is in said second position; and
- means to prevent movement of said body from said second position to said first position.

There is further disclosed herein a valve assembly for a syringe having an interacting piston and cylinder, with the cylinder terminating at one end with a mounting to receive a syringe needle, said piston and cylinder co-operating to define a variable volume working chamber which receives a liquid to be injected by the syringe, said valve assembly being adapted to be located within said chamber so as to divide said chamber into a first sub-chamber located adjacent the needle mounting, and a second sub-chamber located adjacent the piston, said valve assembly including a valve sleeve to be sealingly received within said cylinder so as to be coaxial with respect thereto, said sleeve having an internal peripheral surface;

a movable valve member received within said sleeve and sealingly co-operating therewith so that in use of the syringe the valve member selectively controls the direction of flow of liquid within the syringe, said valve member having a pair of axially spaced annular sealing surfaces which sealingly engage said sleeve, and which are resiliently deformable;

a first set of sleeve projections extending inwardly of said sleeve to engage a first one of said sealing surfaces;

a second set of sleeve projections extending inwardly of said sleeve to engage the other sealing surface, said second set of sleeve projections being spaced longitudinally of said first set of sleeve projections; and wherein said valve member is longitudinally movable between a first [portion] *position* wherein the first annular sealing surface is engaged with the first set of sleeve projections so as to be deformed and deflected from said sleeve so that liquid may pass thereby, and the other sealing surface is in sealing contact with said sleeve and inhibits the direction of fluid flow in a first direction, and a second position wherein said second sealing surface is engaged with said second set of sleeve projections so that liquid may pass thereby, and said first sealing surface is sealingly engaged with said sleeve to inhibit fluid flow in a second direction, which is opposite to said first direction.

*FURTHER DISCLOSURE*

A preferred form of the present invention will now be described by way of example with reference to accompanying drawings, wherein.

Figure 1:
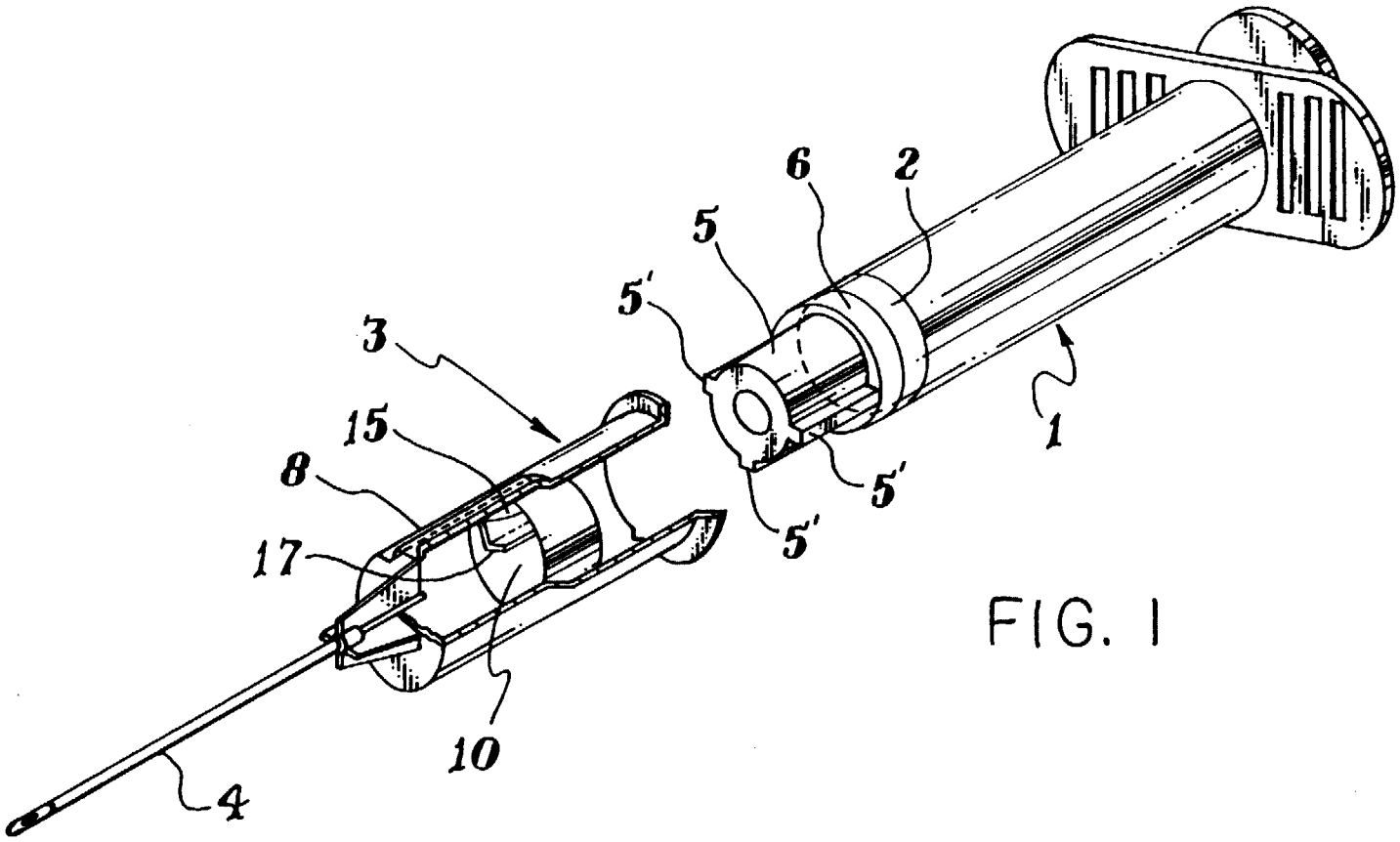
FIG. 1 is a schematic perspective part section view of a single use syringe.

In the preferred embodiment of the invention shown in the FIGS. 1 to 5, the valve has been incorporated in the needle portion 3 of a syringe, the syringe main body portion 1 and needle portion 3 being made preferably as separate pieces. The valve includes a sliding portion 10 comprising a cylindrical body 14, at the opposite ends of which peripheral seals 34 and 36 are provided. Flexible flaps 17 and 19 extend from opposite ends and at diametrically opposed sections from arms 15 and 16 of cylindrical body 14. In co-operation with the wall 13 of the syringe, flap 19 acts as an inlet valve while the flap 17 acts as an outlet valve in a manner to be described below.

The wall 13 includes two outwardly extending portions 8 and 9. Portion 8 has a sloping portion extending from point 24 to point 32 to provide channel 18. The portion 9 has a sloping portion from point 22 to point 23 to provide channel 21. The wall 13 is also provided with a portion 28 extending towards the needle 4 from point 22, ending in a shoulder 25 which forms a stop for the body 14 in a manner to be explained below.

Figure 2:
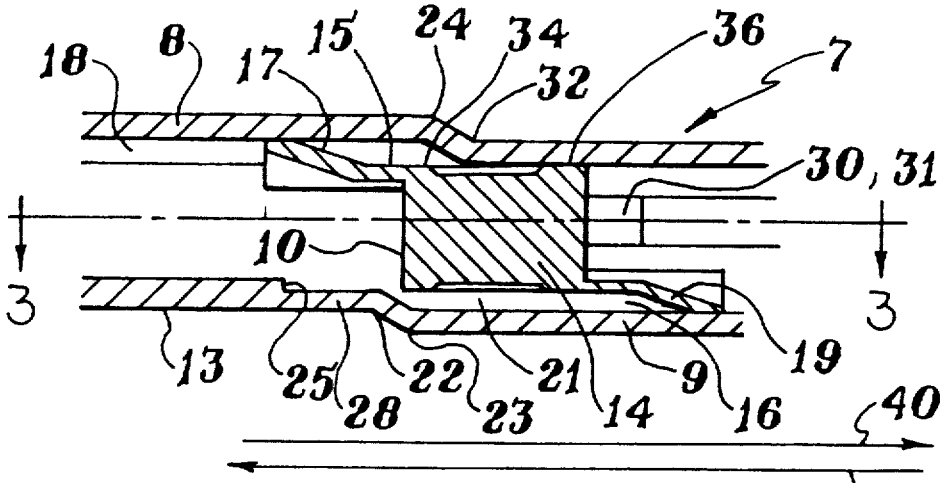
FIG. 2 is a schematic section side elevation of a portion of the syringe of FIG. 1 in a first operative mode.

The flaps 17 and 19 are made of such a resilient material that in their resting state as shown in FIG. 2 they lie against the wall 13. The flaps 17 and 19 as shown in FIGS. 1.], 2 and 4 are shaped so as to provide a sealing action not only against wall 13 within channels 18 and 21 but also against the side walls of these channels.

Figure 3:
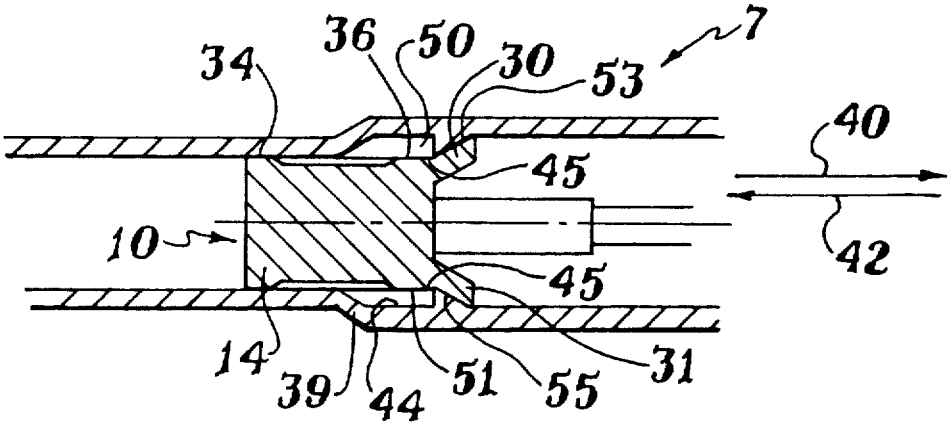
FIG. 3 is a schematic sectioned side elevation of the syringe portion of FIG. 2.

At approximately right angles to the flaps 17 and [19a] *19, a* pair of fingers 30 and 31 is provided as best shown in FIG. 3. These fingers extend from the body 14 near seal means 36 and at the end of sliding portion 10 distal of the needle tip 4. Fingers 30 and 31 extend into channels 50 and 51, which are interrupted by inclined surfaces 53 and 55 which lead to forwardly facing shoulders 45. The fingers 30 and 31 are suitably resilient to enable them to bend upon motion of the sliding portion 10 in the forward direction of arrow 42 so that upon passing the shoulder 45 they re-enter the channels 50 and 51 and thereby prevent return movement of the valve body 10. In addition, the fingers 30 and 31 help to centre (*center*) the body 10 within the wall 13, for example, by seating against the inclined surfaces 53 and *55* in their initial state.

The operation of the valve will now be described with particular reference to FIGS 2, 3 and 4. The drawing of fluid into the needle 4 in the direction of arrow 40 will cause the flap 19 to move away from the wall in the channel 21, allowing fluid past the cylindrical body 14 via channel 21. The flap 19 will remain open as long as the [filing] *filling* stroke continues.

Once the desired dose has been drawn up, the plunger 2 is moved in the direction of arrow 42. This initiates an expulsion stroke. The pressure of fluid being forced in the direction of arrow 42 by the plunger 2 in the main body portion 1 of the syringe causes the flap 19 to seat against the surface of the fixed portion 13. The cylindrical part 14 is driven in the direction of arrow 42 by fluid pressure. This forces the seal 34 of the body 14 against point 22 to completely close channel 21 while dragging flap 14 therealong. Further motion in the direction of arrow 42 can continue until the body 14 presses against [should] *shoulder* 25 thereby (FIG. 4).

Once the seal 36 of the cylindrical part 14 has cleared the point 32, fluid pressure will open the flap 17 to allow expulsion of fluid through the needle top portion 4. Concurrently, the fingers 30 and 31 become engaged forward of the shoulders 45. The expulsion stroke of the syringe is completed as desired.

Refilling of the syringe is now prevented. Flap *17* will allow expulsion of the contents of a syringe, but upon initiation of a stroke in the direction of arrow 40 and flap 17 will engage the wall 13, preventing the filling of the syringe, while the body 14 moves slightly in the direction of arrow 40 until engagement of the fingers 30 and 31 with the shoulders 45 prevents further movement of the body 14. The body 14 is then located with the seal 36 in contact with the wall 13 at point 32 so that the flow of fluid in the direction of arrow 40 is prevented. This effectively limits the syringe having these valve means to being used for *a* single filling and expulsion stroke.

The material used for the body 14, the flaps 17[,] *and* 19, and the fingers 30 and 31 may be any suitably resilient and pharmacologically acceptable material such as [non-prene] *neoprene*.

Figure 5:
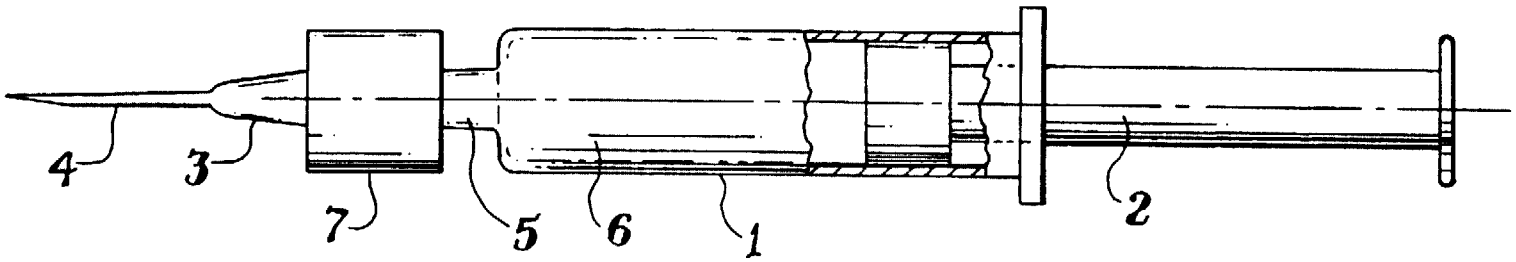
FIG. 5 is a schematic side elevation of an alternative syringe to that shown in FIG. 1.
Figure 7:
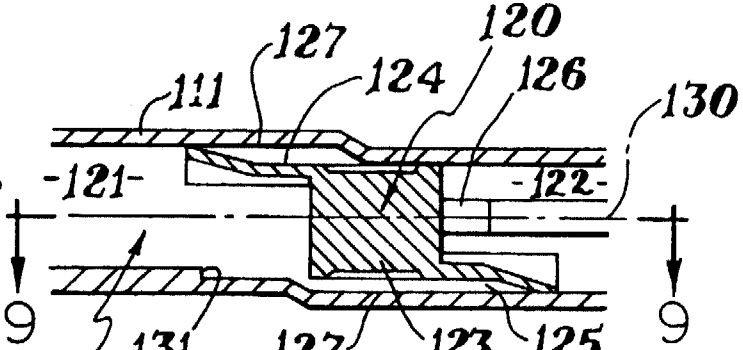
FIG. 7 is a schematic sectioned side elevation of a portion of the syringe of FIG. 6, with the syringe in a first mode of operation.
Figure 9:
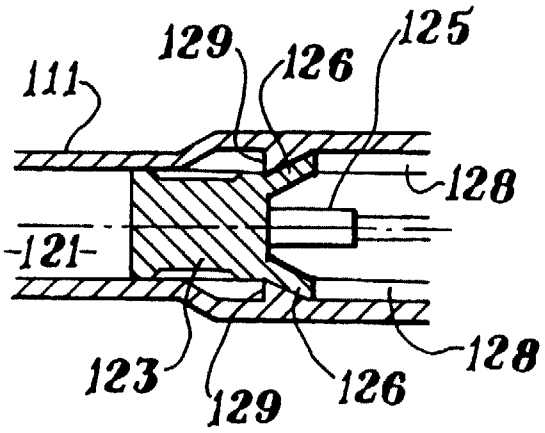
FIG. 9 is a schematic sectioned side elevation of the portion of FIG. 7 sectioned along the line 9—9.
Figure 8:
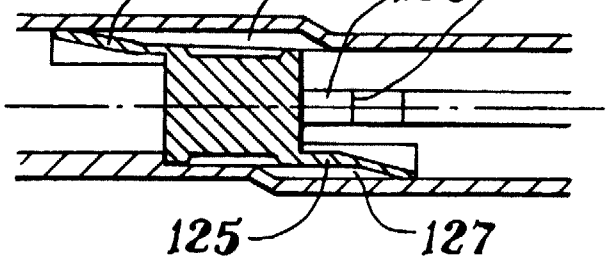
FIG. 8 is a schematic sectioned side elevation of the portion of FIG. 7, with the syringe in a second mode of operation.
Figure 6:
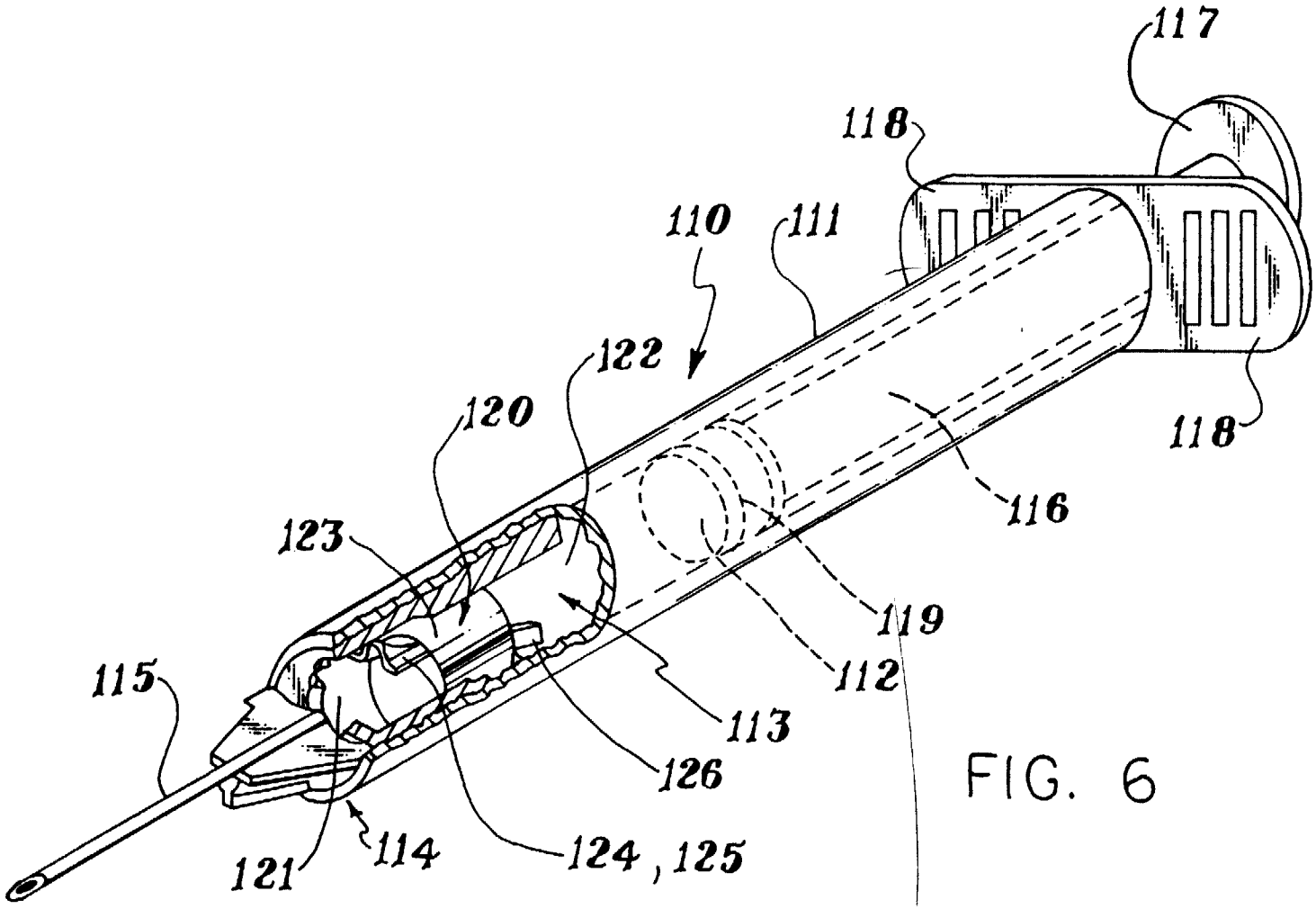
FIG. 6 is a schematic part sectioned perspective view of a single use syringe.
Figure 10:
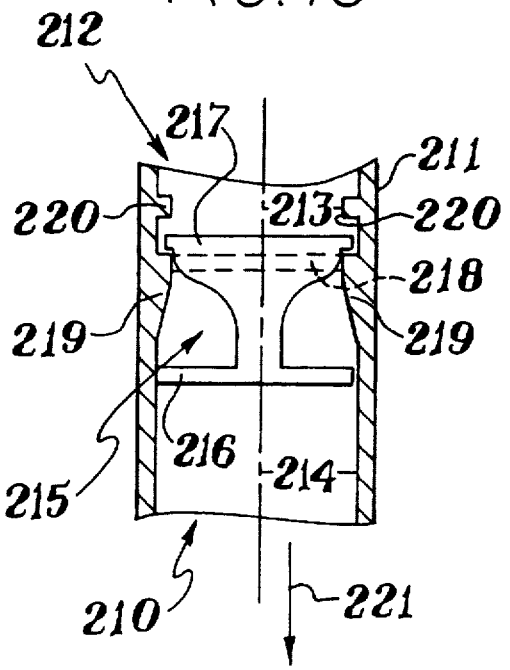
FIG. 10 is a schematic sectioned side elevation of a portion of a syringe.

Though the preferred embodiment shows the invention in the needle portion of a syringe, other ways of carrying out the invention are also contemplated. For example, the valve means of the invention can be provided in the neck portion 5, the end portion of the main body portion 1, or in a needle portion 3 integral with the main body of a syringe. The valve means can also be provided as a separate module in any of the portions 3, 5 or 6, or as a module which is securely fixed at manufacture intermediate the neck portion 5 and the needle portion 3 of a syringe, as illustrated in FIG. 5. The main body portion 1, the valve means 7, and the needle portion 3, in the latter [thereby forming] *case, form* a single integral unit. Equally, the valve means 7 can be fixed to the neck portion 5, or *to* the needle portion 3, separately, for cooperation with a needle portion 3 or a neck portion 5, respectively, of a syringe.

When the valve means is used as a separate module within region 6 of the main body portion 1 of a syringe, it is to be understood that the module can be inserted as a plug, the size of which can be [standardised] (*standardized*) and fitted to variously sized syringes by sleeves or other suitable fixing or securing means.

In any of the above situations there is a [possibilitly] *possibility* that the syringe may be re-usable if the plunger portion 2 is withdrawn and the syringe filled from the rear. To prevent this situation the rear end of the main body portion 1 through which the plunger is inserted can be crimped or heat staked after the plunger has been inserted at manufacture.

Equally, stop means can be provided to prevent false operation of the valve means during transit.

In FIGS. 6 to 9 of the accompanying drawings there is schematically depicted a syringe 110 comprising an interacting cylinder 111 and piston 112 which co-operate to define a sealed chamber 113. The leading portion of the cylinder 12 is closed by a needle mounting 114 which receives a syringe needle 115.

Extending rearwardly from the piston 112 is a piston rod 116 extending to an end flange 117. The end of the cylinder 111 is provided with a pair of flanges 118 which are gripped by the user together with the flange 117. The piston 112 is provided with one or more sealing rings 119.

Located within the chamber 113 is a movable valve member 120 which is slidably received by the internal cylindrical surface of the cylinder 111, and *which* divides the chamber 113 into two sub-chambers 121 and 122. The sub-chamber 121 [being] *is* located adjacent the needle mounting 114[,] while the sub-chamber 122 is located between the piston 112 and the valve assembly 120.

The valve member 120 includes a main body 123 upon which there is mounted a pair of valve flaps 124 and 125 as well as a pair of pawl members 126.

The internal peripheral surface of the cylinder 111 is provided with shaped recesses 127 which slidably receive the valve flaps 125, and shaped recesses 128 which receive the pawl members 126.

The internal peripheral surface of the cylinder 111 is also provided with abutments 129 which are positioned to be engaged by the pawl members 126.

The valve member 120 is longitudinally slidably movable within the cylinder 111 so as to be movable between a first operative position as shown in FIG. [2] *7*, and a second operative position as shown in FIG. [3] *8*. In the operative position of FIG. [2] *7*, a user of the syringe can increase the volume of the chamber 113 by moving the piston away from the needle [113] *115*. A liquid is then drawn in through the needle *115* into the chamber 113 and is allowed to pass between the sub-chambers 121 and 122 via inward deflection of the valve flap 125. The valve flap 125 deflects towards the longitudinal axis [30] *130* of the cylinder 111. Once a desired amount of liquid has been drawn into the syringe 110, the needle 115 is inserted, and the piston 112 *is* moved towards the needle 115. As the pressure of in the [chamber] *sub-chamber* 122 increases, the valve flap 125 is forced into sealing engagement with the internal peripheral surface of the cylinder 111. This pressure further causes movement of the valve member 120 towards the needle 115 until the body 123 abuts a step 131, as shown in FIG. [3] *8*. Further movement of the piston 112 then causes the liquid to move past the body 123 to cause inward deflection of the valve flap 124 towards the longitudinal axis 130.

In the position shown in FIG. [3] *8*, it should be appreciated that the body 123 is in sealing engagement with the internal peripheral surface of the cylinder 111 apart from the recess 127 which is selectively closed by the valve flap 124.

When the valve assembly 120 is in the position shown by FIG. [3] *8*, the pawl members 126 are located forward of the abutments 129. Accordingly, if an attempt is made to re-use the syringe by again moving the piston 112 away from the needle 115, the valve member will not return to the position as shown in FIG. [2] *7*. However, while in the position of FIG. [3] *8*, the valve flap 124 prohibits liquid being drawn into the chamber 113, and [therefor] *therefore*, the sub-chamber 122 is sealingly cut off from the sub-chamber 121.

It is desirable in some instances to ensure (*insure*) that the needle [25] *115* has been correctly located by drawing into the syringe 110 a small amount of blood. This is done after the syringe *110* has been filled with a liquid to be injected. To provide for this, the step 131 is located relative to the abutments 129 such that a small movement of the valve member 120 away from the needle 115 is possible until the pawl members [26] *126* engage the abutments 129.

In FIGS. [210] *10* and [211] *11* of the accompanying drawings, there is schematically depicted a portion 210 of a syringe. The syringe includes a cylindrical wall [111] *211* which sealingly slidably receives a piston [which is not](*not* illustrated (*unillustrated*)). One end of the chamber 212 is closed by the piston[,] while the other end of the chamber 212 is closed by the piston[,] while the other end of the chamber 212 is closed by a needle mounting (*unillustrated*). The chamber 212 is divided into two sub-chambers 213 and 214 by means of a valve member 215. The valve member 215 is formed of flexible resilient material and is provided with a first flexible end wall 216, and *with* a second end wall 217.

The cylindrical wall 211 has an internal peripheral surface provided with an annular lip 218 and at least one longitudinally extending projection 219. The projections 219 extend longitudinally from this lip 218 towards the piston.

Located forward from the lip 218, towards the needle mounting, is at least one projection 220.

In operation of the syringe described with reference to FIGS. [1] *10* and [2] *11*, initially the valve member 215 is located engaged by the projections 219 so that the end wall 217 is at least partly deformed, as best seen in FIG. [2] *11*. The piston is also located so that the chamber 212 has a minimum volume. Thereafter, a liquid to be injected is drawn into the syringe by the piston being moved away from the valve member 215 in the direction of the arrow 221. Once the desired amount of liquid is contained within the syringe, the needle is oriented vertically, and air *is* expelled from within the syringe. It should be appreciated that the vast majority of the liquid to be injected is located ion the sub-chamber 214. The liquid is allowed to enter the sub-chamber 214 by passing around the deformed end wall 217 and causing deflection of the end wall 216.

Once the desired amount of liquid is located in the syringe, the needle is oriented vertically, and air *is* expelled from within the syringe. This operation will move the valve member 215 to a position located closer to the needle mounting. More particularly, the end wall 217 is moved from engagement with the projections 219, and abuts the projections 220. When in this position, the end wall 216 is engaged by the projections 219. It should be appreciated that this forward movement of the valve member 215 is caused by the pressure within the liquid, applied against the end wall 216.

Further use of the syringe, by movement of the piston again in the direction of the arrow 221 is prevented by the valve member 215 being moved in the direction of the arrow 221 until the valve member *215* sealingly engages the annular lip 218. Since insufficient force and be applied to the valve member 215 to cause deformation thereof by engagement with the projections 219, further use of the syringe is inhibited.

It should be appreciated that the projections 220 ar e spaced from the projections 219 so that a certain amount of movement of the valve member 215 is permitted until the end wall 217 sealingly contacts the lip 218. This enables the syringe needle to be inserted in a vein and the piston drawn back, a limited amount, to draw in a small quantity of blood to thereby detect whether the syringe needle has been correctly inserted.

In FIGS. [3] *12* and [4] *13* there is schematically depicted a portion 230 of a syringe. In this particular embodiment, the syringe has a cylindrical wall 231 encompassing a chamber 232. The chamber is closed at one end by means of a piston[,] (*unillustrated*) while the other end is closed by a needle mounting (*unillustrated*).

The chamber 232 is divided into two sub-chambers 233 and 234 by means of a valve member 235. The valve member 235 is formed of flexible resilient material and has a pair of end walls 236 and 237. The end walls 236 and 237 are joined by a stem 238.

The internal peripheral surface of the wall 231 is provided with an annular lip 239 as well as at least one longitudinally extending projection 240.

Figure 12:
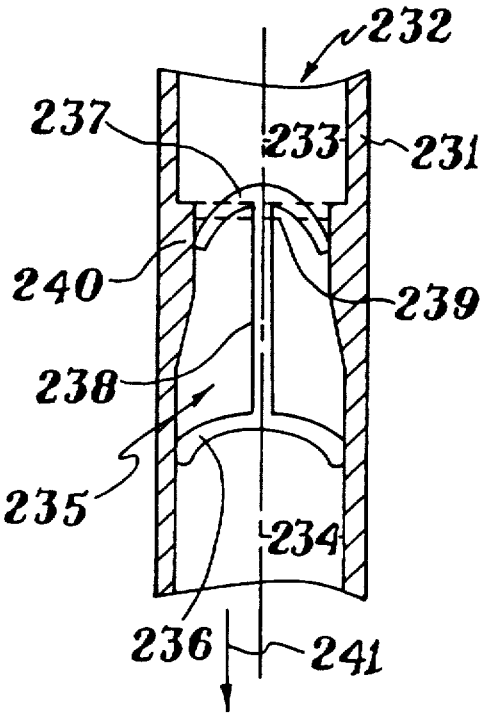
FIG. 12 is a schematic side elevation of a further syringe portion.
Figure 11:
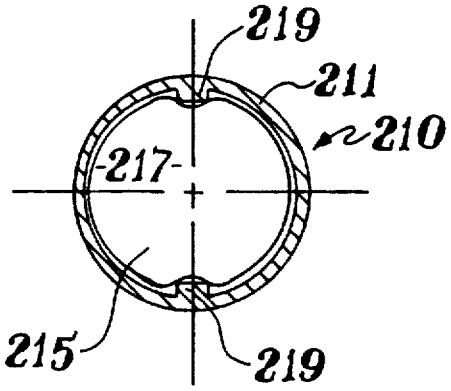
FIG. 11 is a schematic end elevation of the portion of FIG. 10.
Figure 13:
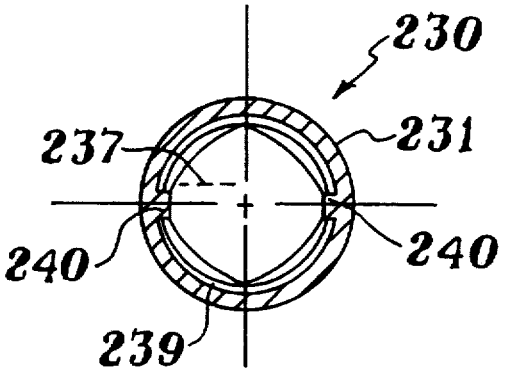
FIG. 13 is a schematic end elevation of the portion of FIG. 12.

In the position depicted in FIGS. 12 and 13, the end wall [217] *237* is engaging the projections 240 so as to be deformed thereby.

Initially, the valve member 235 is located in the position depicted in FIG. [3] *12*. The piston is located so that the volume of the chamber 232 is minimized. To draw a liquid into the syringe, the piston is moved in the direction of the arrow 241 away from the valve member 235. The liquid is drawn into the sub-chamber 234 via movement of the liquid past the end wall 237, due to its deformation, and *to* the deflection of the end wall 236 away from the cylindrical wall 231. Once the desired amount of liquid has been drawn into the syringe, the needle is oriented vertically and air *is* expelled. Movement of the piston to achieve this[,] moves the valve member 235 to a position such that the end wall 237 is forward of the projections 240. However, the end wall 236 is engaged by the projections 240 and is deformed to enable liquid [tc] *to* pass thereby and between the end wall 237 and the internal peripheral surface of the cylindrical wall 231.

Once the needle has been inserted, the piston is moved so as to mimimize the volume of the chamber 232 with the liquid again passing by the deformed end wall 236 and past the end wall 237.

Re-use of the syringe is inhibited since movement of the piston again in the direction 241 moves the valve member 235 to bring the end wall 237 back into sealing contact with the annular lip 239.

The valve member 235 is permitted a certain degree of movement before the end wall 237 is moved back into sealing contact with the annular lip 239, to enable the syringe to be inserted and a smaller amount of blood drawn into the syringe to indicate whether the needle has been correctly located.

In FIGS. 14 to 17 of the accompanying drawings there is schismatically depicted a valve assembly 310 to be mounted within the end portion 311 of a syringe. The end portion 311 includes a needle mounting 312 to receive a syringe needle 313. The end portion 311 includes a generally cylindrical section 314, which if need be may be slightly tapered so as to be "frustoconical" in configuration. Extending from the cylindrical portion 314 is the main body 315 of the syringe which slidably sealingly receives the piston (not illustrated).

The cylindrical section 314 receives the valve assembly 310. The valve assembly 310 includes a valve sleeve 316 which has an outer peripheral surface sealingly mated with the internal peripheral surface of the cylindrical section 314. The internal peripheral surface 317 slidably receives a movable valve member 318. The valve member 318 is of a unitary construction, and *it* is preferably moulded (*molded*) or formed from a resilient elastic material. The valve member 318 has a pair of annular sealing flanges 319 and 320 which provide sealing surfaces which slidably engage the surface 317.

The surface 317 is provided with two sets of projections 321 and 322, with the set of projections 321 being located closer to the needle than the second set of projections 322. The first set of projections 321 [include] *includes* two projections which are located on diametrically opposite sides of the surface 317, and *which* are coextensive and parallel. The second set of projections 322 [which are], *longitudinally spaced from the first set of projections 321 toward the rear of the syringe, also* [include] *includes* a pair of projections, which are located on diametrically opposite sided of the surface 317, and *which* are coextensive and parallel. The projections 322 are spaced [390] *at 90* degrees angularly about the longitudinal axis 331, from the projections 321.

As best seen in FIGS. [1] *14* and [3] *16*, each of the projections 321 and 322 has a leading face 323 which may be generally normal to the surface 317, or *which may be* slightly inclined thereto so as to provide a barb which will engage the movable valve member 318. The rear end of each projection *set* 321 and 322 is provided by a ramp surface 324.

The valve member 318 is provided with an annular recess 325 with a leading surface 326. The recess 325 has a rear surface 327. The surface 326 extends generally normal to the longitudinal axis 331[,] while the surface 327 is inclined to the axis 331 by an acute angle.

Each of the projections 321 is provided with a longitudinally extending passage 328 through which a liquid to be injected may pass.

Figure 4:
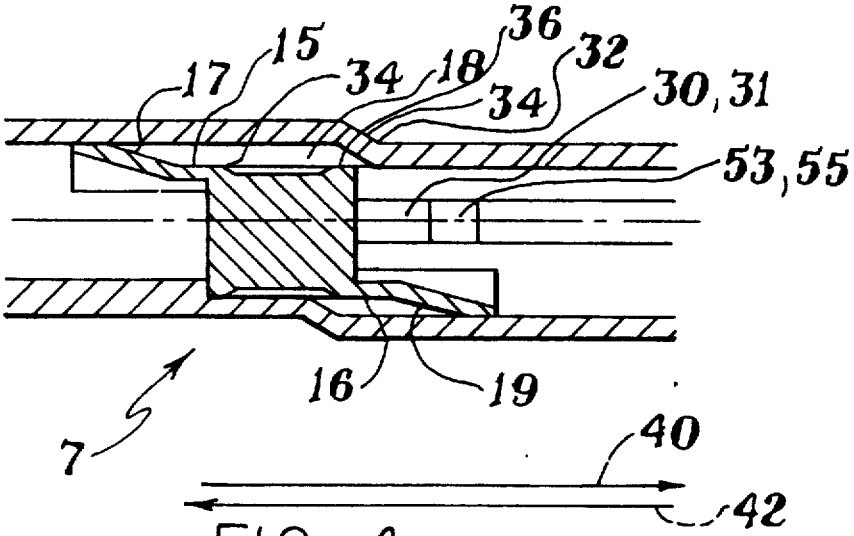
FIG. 4 is a schematic sectioned side elevation of the syringe portion of FIG. 2 in a second operative position.
Figure 14:
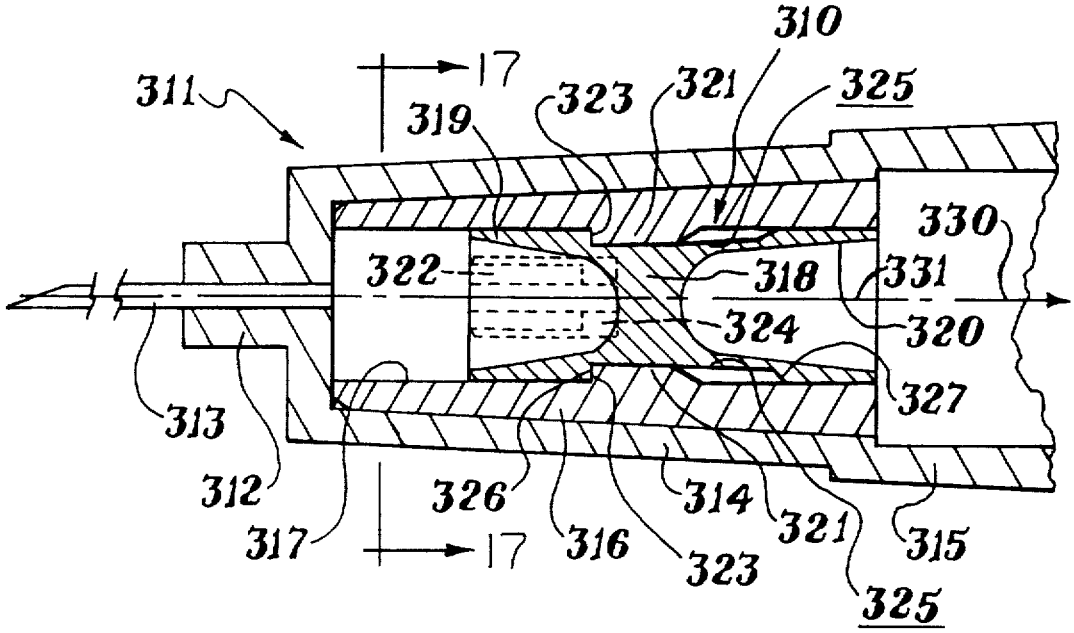
FIG. 14 is a schematic part sectioned side elevation of a valve assembly of a single use syringe, with the valve member thereof in a first operative position.
Figure 15:
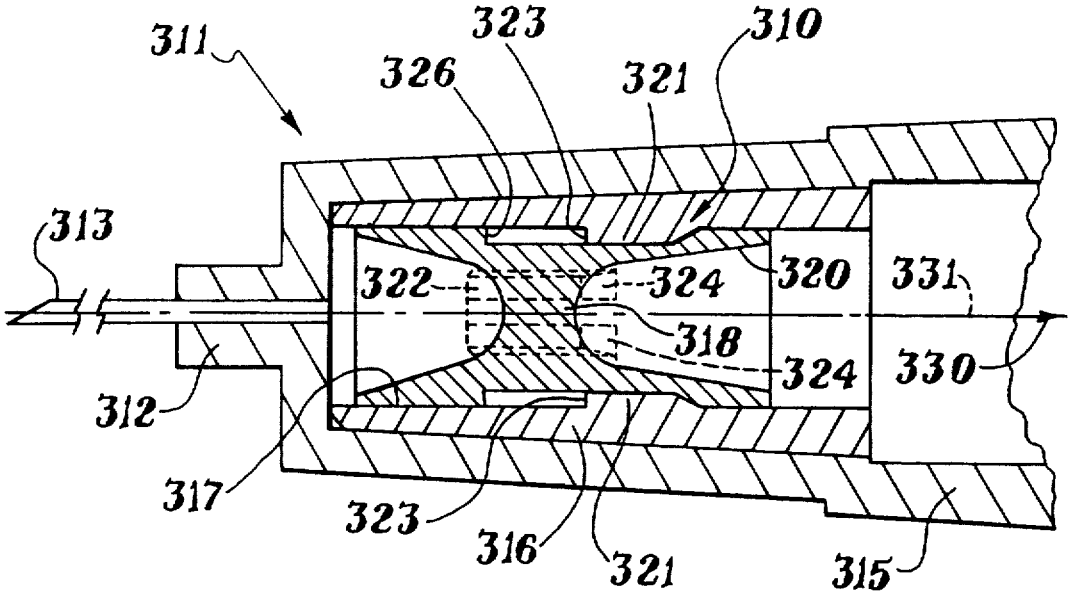
FIG. 15 is a schematic part sectioned side elevation of the valve assembly of FIG. 14, with the valve member in a second operative position.
Figure 16:
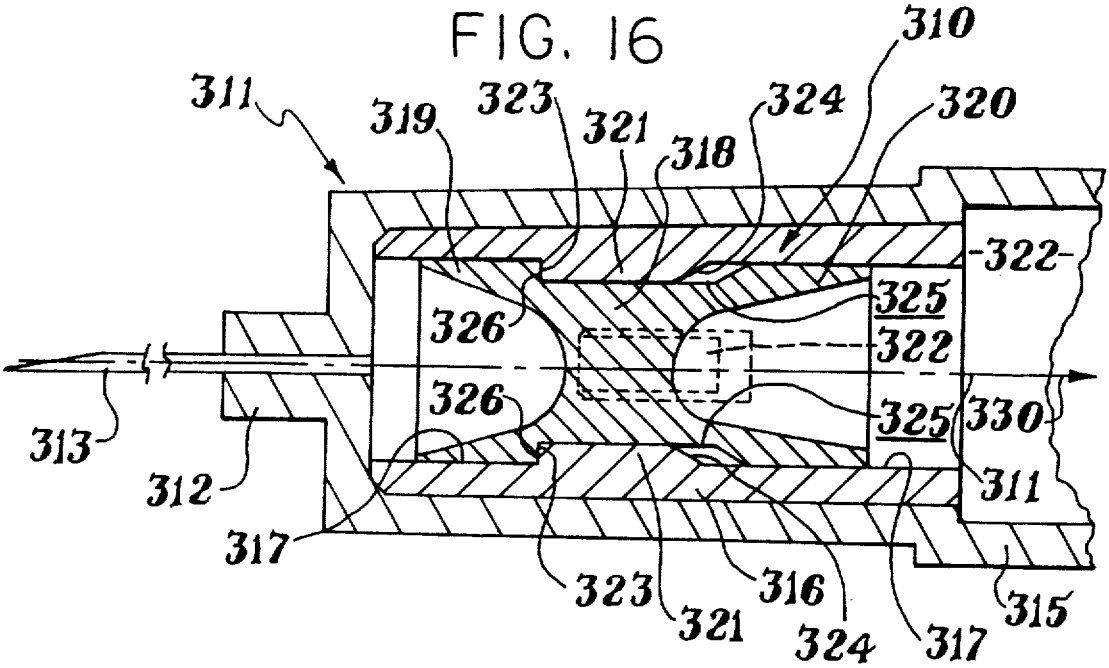
FIG. 16 is a schematic part sectioned side elevation of the valve assembly of FIG. 14, with the valve member in a third operative position.
Figure 17:
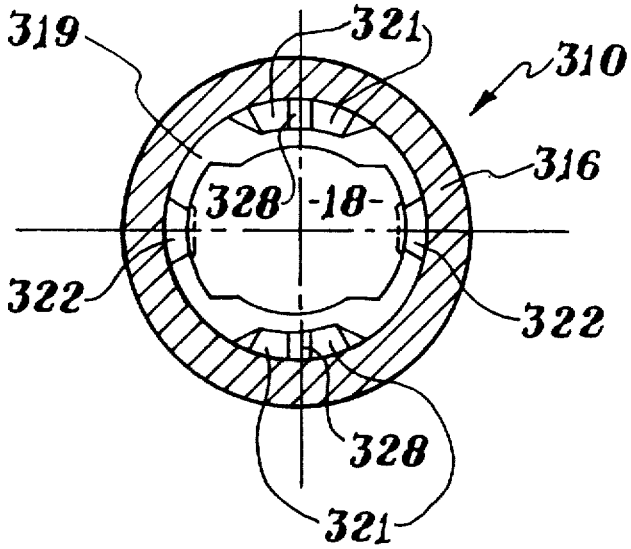
FIG. 17 is a schematic part sectioned end elevation of the valve assembly of FIG. 14 sectioned along the line 17—17.

In operation of the above described valve assembly 310, the movable valve member 318 begins in a starting position as seen in [FIGS. 1 and 4] *FIG. 14*. The projections 321 are engaged with the flange 319 so that the flange 319 is resiliently deformed so that portions thereof are spaced from the surface 317 so that the flange 319 is no longer in sealing contact with the surface 317. When the piston of the syringe is located adjacent the valve assembly 310 and moved in the direction of the arrow 330, a liquid is drawn in through the needle 313, [pass] *past* the flange 319, and, due to the pressure differential across the flange 320, the flange 320 deflects from a sealing contact with the surface 317, [and] *which* permits the liquid to enter the main chamber 332 of the syringe. When the desired amount or liquid has been drawn into the syringe, and the operator wishes to expel any air contained in the syringe, the needle 313 is placed so as to extend vertically. Thereafter, any air contained in the syringe will move upwardly. The operator then moves the piston or plunger to expel the air. When the piston moves, the pressure [within] *of* the liquid within the chamber 331 causes the valve member 318 to move towards the needle 313[,] so that the flange 319 moves from operative contact with the projections [321] *322*. When this occurs, the flange 320 moves in contact with the projections [322] *321*. Accordingly, the flange [320] *319* is moved from sealing contact with the surface 317. The liquid then is able to pass the flange 320 and cause deflection of the flange 320 to pass towards the needle 313. This position is shown in FIG. [2] *15*.

In some instances it is desirable to test to determine whether the needle has been correctly inserted. This is achieved by drawing back on the piston and drawing into the syringe a small amount of blood. This test can be carried out due to the distance between the surface 326 and the surface 323, which distance[,] permits a small amount of rearward movement of valve member 318. When the piston is drawn back, the movable valve member 318 moves until the surface 326 engages the surfaces 323 of the projections 321. Once this has occurred, the movable valve member 318 is prevented from any further rearward movement. Once in this position, the flanges 319 are in sealing contact with the surface 317 and prevent any further material being drawn into the syringe. To inject the liquid contained within the chamber 332, again the piston is moved forward towards the needle 313 [and past the flanges 320 (as they are deformed by the projections 322)]. The pressure [in] *of* the liquid then deflects the flanges 319 away from the surface 317 so that the liquid can then reach the [needles] *needle* 313.

Re-use of the syringe is inhibited since once the syringe has been used, the surface 326 is located forward of the surfaces 323 of the projections 321. Once this has occurred, the valve member 318 prevents any liquid being drawn into the chamber 332.

We claim:

1. A single use syringe comprising:

an inter-acting piston and cylinder defining a variable chamber within which a liquid to be injected is drawn;

a needle mounting at one end of said cylinder, to receive a needle, a passage extending through said mounting enabling liquid communication between said [cylinder] *chamber* and said needle;

a piston rod attached to said piston and operable by a user to cause movement of said piston to vary the volume of said chamber;

a valve means including a valve body located within said chamber between said mounting and said piston and dividing said chamber into a first sub-chamber located between said mounting and valve means[,] and a second sub-chamber located between said valve means and said piston, said valve body being movable longitudinally of said cylinder between a first position and a second position, [and] *wherein* said valve means includes *1)* a first valve which, when said *valve* body is in said first position, permits flow from said first sub-chamber to said second sub-chamber and prevents flow from said second sub-chamber to said first sub-chamber, but when said *valve* body is in said second position, said first valve permits flow form said second sub-chamber to said first sub-chamber [and prevents flow from said first sub-chamber to said second sub-chamber,], *and 2)* a second valve which, when said *valve* body is in said first position, permits flow from said first sub-chamber to said second sub-chamber, but prevents flow from said first sub-chamber to said second sub-chamber when said *valve* body is in said second position[;], and means to prevent movement of said *valve* body from said second position to said first position.

2. The syringe of claim 1, wherein said [first] *second* position of said *valve* body is closer to said mounting than [the second] *said first* position of said *valve* body.

3. The syringe of claim 1 or 2, wherein said first and second valves include valve flaps attached to said *valve* body, and said cylinder has recesses selectively sealingly cooperating with said valve flaps.

4. The syringe of claim [2,] *3* further including first projection means to engage the valve flap of said first valve, which first projection means is positioned to deflect said valve flap from sealing engagement with said cylinder when said *valve* body is in said second position, and second projection means to engage [thje] *the* valve flap of said second valve means to move it from sealing contact with said cylinder when said *valve* body is in said first position.

5. The syringe of claim 1 *or 2,* wherein said valve body is formed of resilient material, and said valves include resilient [annular] flanges on said *valve* body, and a first projection means on said cylinder [and] positioned to engage [the flap] *the flange* of [the] *said* first valve when said *valve* body is in said second position, and second projection means which engages the flange of said second valve when said *valve* body is in said first position, *further wherein said flanges are circular.*

6. A valve assembly for a syringe having an interacting piston and cylinder, with the cylinder terminating at one end with a mounting to receive a syringe needle, said piston and cylinder co-operating to define a variable volume working chamber which receives a liquid to be injected by the syringe, said valve assembly being adapted to be located within said chamber so as to divide said chamber into a first sub-chamber located adjacent the needle mounting[.] and a second sub-chamber located adjacent the piston, said valve assembly ]including;] *comprising the following components:* a valve sleeve to be sealingly received within said cylinder so as to be coaxial with respect thereto, said sleeve having an internal peripheral surface;

a movable valve member received within said sleeve and sealingly co-operating therewith so that in use of the syringe the valve member selectively controls the direction of flow of liquid within the syringe, said valve member having a pair of axially spaced [annular] *circular* sealing surfaces which sealingly engage said sleeve, and which are resiliently deformed;

a first set of sleeve projections extending inwardly of said sleeve to engage a first one of said sealing surfaces[;]. *and* a second set of sleeve projections extending inwardly of said sleeve to engage the other sealing surface, said second set of sleeve projections being spaced longitudinally of said first set of sleeve projections[; and], wherein said valve member is longitudinally movable between a first [portion] *position* wherein the first [annular]sealing surface is engaged with [the] *said* first set of sleeve projections so as to be deformed and deflected from said sleeve so that liquid may pass thereby, and the other sealing surface is in sealing contact with said sleeve and inhibits [the direction of] fluid flow in a first direction, and a second position wherein [said] *the* second sealing surface is engaged with said second set of sleeve projections so that liquid may pass thereby, and said first sealing surface is sealingly engaged with said sleeve to inhibit fluid flow in a second direction[, which is] opposite to said first direction.

7. A single use syringe [having] *comprising* an interacting piston and cylinder, with the cylinder terminating at one end with a mounting to receive a syringe needle, said piston and cylinder cooperating to define a variable volume working chamber which receives a liquid to be injected by the syringe, and [the] *a* valve assembly [of claim 6], which valve assembly is located within said chamber so as to divide said chamber into [said] *a* first sub-chamber and [said] *a* second sub-chamber, *and which valve assembly includes the following components:*

*a valve sleeve to be sealingly received within said cylinder so as to be coaxial with respect thereto, said sleeve having an internal peripheral surface;*

*a movable valve member received within said sleeve and sealingly co-operating therewith so that in use of the syringe the valve member selectively controls the direction of flow of liquid within the syringe, said valve member having a pair of axially spaced circular sealing surfaces which sealingly engage said sleeve, and which are resiliently deformed;*

*a first set of sleeve projections extending inwardly of said sleeve to engage a first one of said sealing surfaces, and*

*a second set of sleeve projections extending inwardly of said sleeve to engage the other sealing surface, said second set of sleeve projections being spaced longitudinally of said first set of sleeve projections,*

*wherein said valve member is longitudinally movable between a first position wherein the first sealing surface is engaged with said first set of sleeve projections so as to be deformed and deflected from said sleeve so that liquid may pass thereby, and the other sealing surface is in sealing contact with said sleeve and inhibits fluid flow in a first direction, and a second position wherein the second sealing surface is engaged with said second set of sleeve projections so that liquid may pass thereby, and said first sealing surface is sealingly engaged with said sleeve to inhibit fluid flow in a second direction opposite to said first direction.*

*8. A valve for a single use syringe having an interacting piston and cylinder and a syringe needle, said valve comprising:*

*duct means providing a passage through which liquid to be injected must pass to be delivered to said needle;*

*a movable valve body located in said duct means and dividing said passage into a first sub-chamber and a second sub-chamber with, said first sub-chamber to be located closer to said needle than said second sub-chamber, said valve body being movable longitudinally of said duct means between a first position and a second position under the influence of pressure applied thereto through said liquid, wherein said valve body includes 1) a first valve means sealingly co-operating with said duct means, which, when said valve body is in said first position, permits flow from said first sub-chamber to said second sub-chamber and prevents flow from said second sub-chamber to said first sub-chamber, but which, when said valve body is in said second position, permits flow from said second sub-chamber to said first sub-chamber, and 2) a second valve means which, when said valve body is in said first position, permits flow from said first sub-chamber to said second sub-chamber, but which, when said body is in said second position, prevents flow from said first sub-chamber to said second sub-chamber, and* means to prevent movement of said valve body from said second position to said first position.

9. The valve of claim 8, wherein said second position of said valve body is intended to be closer to said needle than said first position of said valve body.

10. The valve of claim 8 or 9, wherein said first and second valve means include valve flaps attached to a central portion of said valve body, and said duct means has recesses selectively sealingly co-operating with said valve flaps.

11. The valve of claim 9, wherein said valve body is formed of resilient material, and each of said valve means includes a resilient circular flange, and said each of said valve means further includes projection means on an internal peripheral surface of a sleeve positioned to engage said first valve means when said valve body is in said second position and to engage said second valve means when said valve body is in said first position.

12. The valve of claim 11, wherein said projection means includes 1) first projection means to engage said first valve means, positioned to deflect said first valve means from sealing engagement with said duct means when said valve body is in said second position, and 2) second projection means to engage said second valve means to move it from sealing contact with said duct means when said valve body is in said first position.

13. The valve of claim 9, wherein said piston and cylinder provide a primary chamber;

said valve is adapted to be located within said primary chamber so as to divide said primary chamber into said first sub-chamber, which is located adjacent the needle mounting, and said second sub-chamber, which is located adjacent said piston, and said valve is sealingly received within said cylinder so as to be coaxial with respect thereto.

14. A single use syringe comprising the following components:

(I) an inter-acting piston and cylinder definirg a variable volume primary chamber within which a liquid to be injected is drawn;

(II) a needle mounting at one end of said cylinder to receive a needle;

(III) a passage extending through said mounting enabling liquid communication between said cylinder and needle;

(IV) a piston rod attached to said piston and operable by a user to cause movement of said piston to vary the volume of said primary chamber, and (V) a valve, through which said liquid must pass in flowing between said needle and primary chamber, which valve includes (A) duct means providing a passage through which liquid to be injected must pass to be delivered to said needle;

(B) a movable valve body located in said duct means and dividing said passage into a first sub-chamber and a second sub-chamber, with said first sub-chamber to be located closer to said needle than said second sub-chamber, said valve body being movable longitudinally of said duct means between a first position and a second position under the influence of pressure applied thereto through said liquid, wherein said valve body includes 1) a first valve means sealingly co-operating with said duct means, which, when said valve body is in said first position, permits flow from said first sub-chamber to said second sub-chamber and prevents flow from said second sub-chamber to said first sub-chamber, but which, when said valve body is in said second position, permits flow from said second sub-chamber to said first sub-chamber, and 2) a second valve means which, when said valve body is in said first position, permits flow from said first sub-chamber to said second sub-chamber, but which, when said body is in said second position, prevents flow from said first sub-chamber to said second sub-chamber, and (C) means to prevent movement of said valve body from said second position to said first position, wherein said second position of said valve body is intended to be closer to said needle than said first position of said valve body.

15. The syringe of claim 14, wherein said valve body is located within said primary chamber between said mounting and piston, and said cylinder provides said passage.

16. The syringe of claim 14, wherein said valve is located in said needle mounting.

17. The valve of claim 8, wherein said second position is intended to be closer to the needle than said first position.

18. The valve of claim 17, characterized in that the flow from said first sub-chamber to said second sub-chamber can charge the syringe with liquid, while the flow from said second sub-chamber to said first sub-chamber provides for injection of the liquid from the syringe.

19. The valve of claim 18, characterized by further including annular seal means surrounding a portion of said passage and wherein said valve body engages one side of said seal means in said first position before being moved longitudinally, under the influence of said pressure, relative said seal means to said second position, at which said valve body engages the other side of said seal means to prevent flow from said first sub-chamber to said second sub-chamber.

20. The valve of claim 19, wherein said first and second valve means are leading and trailing portions of said valve body with respect to movement of said valve body in the direction of movement between said first position and said second position.

21. The valve of claim 20, wherein said means to prevent movement of said valve body from said second position to said first position is in the configuration of said valve body and said seal means.

22. The valve of claim 21, wherein said seal means provides a valve opening through which said valve body passes.

23. The valve of claim 22, wherein resilient deformation permits movement of said valve body through said seal means.

24. The valve of claim 23, wherein said first and second valve means are resilient circular end walls of said valve body, which valve body includes a longitudinal stem joining the end walls.

25. The valve of claim 24, wherein said second valve means co-operates with said seal means to prevent flow from said first sub-chamber to said second sub-chamber when said valve body is in its second position, and said first valve means co-operates with said seal means to prevent flow from said second sub-chamber to said first sub-chamber when said valve body is in its first position.

26. The valve of claim 25, wherein said second valve means is resiliently deformable so as to pass through said valve opening when said valve body is moved from the first position to said second position.

27. The valve of claim 22, wherein said first and second valve means are circular end walls.

28. The valve of claim 19, which further includes annular seal means surrounding a portion of said passage, and projection means to engage said first valve means when said valve body is in said second position, wherein the valve

*means are valve flanges of circular configuration, and said valve body extends through said seal means when said valve body is in either said first or said second position.*

*29. The valve of claim 8 or 18, wherein said first and second valve means are leading and trailing portions of said valve body with respect to movement of the valve body in the direction of movement between said first position and said second position.*

* * * * *